(12) United States Patent
Tanaka et al.

(10) Patent No.: US 9,414,882 B2
(45) Date of Patent: Aug. 16, 2016

(54) TREATMENT SYSTEM AND ACTUATION METHOD FOR TREATMENT SYSTEM

(71) Applicant: OLYMPUS CORPORATION, Tokyo (JP)

(72) Inventors: Kazue Tanaka, Sagamihara (JP); Yoshitaka Honda, Hachioji (JP); Takashi Irisawa, Hachioji (JP); Sadayoshi Takami, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 32 days.

(21) Appl. No.: 13/921,577

(22) Filed: Jun. 19, 2013

(65) Prior Publication Data

US 2013/0338665 A1 Dec. 19, 2013

Related U.S. Application Data

(63) Continuation of application No. PCT/JP2012/079372, filed on Nov. 13, 2012.

(60) Provisional application No. 61/569,333, filed on Dec. 12, 2011.

(51) Int. Cl.
*A61B 18/14* (2006.01)
*A61B 18/08* (2006.01)
(Continued)

(52) U.S. Cl.
CPC .............. *A61B 18/14* (2013.01); *A61B 18/085* (2013.01); *A61B 18/10* (2013.01);
(Continued)

(58) Field of Classification Search
CPC ........... A61B 2018/00589; A61B 2018/00595; A61B 2018/00619; A61B 2018/0063; A61B 2018/00678; A61B 2018/00666; A61B 2018/00708; A61B 2018/00672
USPC ..................... 606/31, 38, 42, 50–52
See application file for complete search history.

(56) References Cited

U.S. PATENT DOCUMENTS 5,540,681 A * 7/1996 Strul et al. ...................... 606/34
6,464,696 B1 10/2002 Oyama et al.
(Continued)

FOREIGN PATENT DOCUMENTS

EP 1 582 165 A1 10/2005
EP 2 106 762 A1 10/2009
(Continued)

OTHER PUBLICATIONS

Extended Supplementary European Search Report dated May 26, 2015 from related European Application No. 12 85 7115.5.

*Primary Examiner* — Jocelyn D Ram
(74) *Attorney, Agent, or Firm* — Scully, Scott, Murphy & Presser, P.C.

(57) ABSTRACT

A treatment system includes a power source for heat generation which outputs power for heat generation, a grasping member having a heating element which applies the power for heat generation as thermal energy to a living tissue, and a control section which performs constant temperature control on the power source for heat generation on the basis of temperature of the heating element, and controls the power source for heat generation so as to finish application of the thermal energy and complete treatment if the power for heat generation becomes not more than predetermined threshold power which is independent of a type of the living tissue or if a rate of decrease in the power for heat generation becomes not more than a predetermined threshold rate.

6 Claims, 9 Drawing Sheets

(51) Int. Cl.
   *A61B 18/10* (2006.01)
   *A61B 18/12* (2006.01)
   *A61B 18/00* (2006.01)

(52) U.S. Cl.
   CPC ........ *A61B 18/1206* (2013.01); *A61B 18/1442* (2013.01); *A61B 18/1445* (2013.01); *A61B 2018/00619* (2013.01); *A61B 2018/00625* (2013.01); *A61B 2018/00642* (2013.01); *A61B 2018/00672* (2013.01); *A61B 2018/00678* (2013.01); *A61B 2018/00702* (2013.01); *A61B 2018/00708* (2013.01); *A61B 2018/00714* (2013.01); *A61B 2018/00761* (2013.01); *A61B 2018/00767* (2013.01); *A61B 2018/00779* (2013.01); *A61B 2018/00791* (2013.01); *A61B 2018/00875* (2013.01); *A61B 2018/00886* (2013.01); *A61B 2018/00994* (2013.01)

(56) References Cited

U.S. PATENT DOCUMENTS

| | | | |
|---|---|---|---|
| 8,632,531 B2* | 1/2014 | Bouthillier et al. | 606/31 |
| 2004/0006337 A1* | 1/2004 | Nasab et al. | 606/41 |
| 2004/0092923 A1* | 5/2004 | Miura et al. | 606/28 |
| 2004/0167508 A1* | 8/2004 | Wham et al. | 606/32 |
| 2004/0193148 A1* | 9/2004 | Wham et al. | 606/40 |
| 2005/0010206 A1* | 1/2005 | Nasab et al. | 606/41 |
| 2005/0222560 A1* | 10/2005 | Kimura et al. | 606/28 |
| 2008/0015575 A1* | 1/2008 | Odom et al. | 606/51 |
| 2009/0076506 A1* | 3/2009 | Baker | 606/51 |
| 2009/0248002 A1* | 10/2009 | Takashino et al. | 606/28 |
| 2010/0185196 A1* | 7/2010 | Sakao et al. | 606/51 |
| 2011/0077629 A1* | 3/2011 | Tanaka et al. | 606/28 |
| 2011/0238062 A1* | 9/2011 | Koss et al. | 606/34 |
| 2012/0101538 A1* | 4/2012 | Ballakur et al. | 607/3 |
| 2012/0265194 A1* | 10/2012 | Podhajsky | 606/34 |
| 2013/0172887 A1* | 7/2013 | Ichikawa et al. | 606/51 |
| 2013/0324995 A1* | 12/2013 | Dresher | 606/33 |
| 2014/0121507 A1* | 5/2014 | Nau, Jr. | 600/427 |
| 2014/0121508 A1* | 5/2014 | Latimer et al. | 600/427 |

FOREIGN PATENT DOCUMENTS

| | | |
|---|---|---|
| EP | 2 491 880 A1 | 8/2012 |
| JP | 2000-245744 A | 9/2000 |
| JP | 2001-269352 A | 10/2001 |
| JP | 2004-159686 A | 6/2004 |
| JP | 2005-253789 A | 9/2005 |
| JP | 2009-247893 A | 10/2009 |
| JP | 2010-538796 A | 12/2010 |
| WO | WO 2009/039179 A1 | 3/2009 |
| WO | WO 2011/064881 | 6/2011 |

* cited by examiner

TREATMENT SYSTEM AND ACTUATION METHOD FOR TREATMENT SYSTEM

CROSS REFERENCE TO RELATED APPLICATION

This application is a continuation application of PCT/JP2012/079372 filed on Nov. 13, 2012 and claims benefit of U.S. Provisional Patent Application No. 61/569,333 filed in the U.S.A. on Dec. 12, 2011, the entire contents of which are incorporated herein by this reference.

BACKGROUND OF THE INVENTION

1. Field of the Invention

Embodiments of the present invention relate to a treatment system including one pair of grasping members which apply thermal energy to a grasped living tissue and an actuation method for the treatment system.

2. Description of the Related Art

U.S. Patent Application Publication No. 2009/076506 discloses a treatment system including one pair of grasping members which apply high-frequency power energy and thermal energy to a grasped living tissue, a high-frequency power source which outputs high-frequency power for applying high-frequency power energy, a power source for heat generation which outputs power for heat generation for applying thermal energy, and a control section which controls the high-frequency power source and the power source for heat generation for switching between application of high-frequency power energy and application of thermal energy.

U.S. Patent Application Publication No. 2009/0248002 discloses a treatment system which first applies high-frequency power energy to a living tissue and then starts application of thermal energy. High-frequency power energy acts to release intracellular components including polymer compounds typified by protein by destroying cell membranes in a living tissue and make the intracellular components uniformed with extracellular components typified by collagen. Such uniforming of a living tissue promotes joining of a living tissue through subsequent application of thermal energy.

For application of thermal energy, a process is known of raising temperature of a heating element to a predetermined temperature on the basis of a sensed temperature and then performing feedback control so as to hold the temperature at the predetermined temperature.

SUMMARY OF THE INVENTION

A treatment system according to an embodiment includes a power source for heat generation which outputs power for heat generation, a grasping member having a heating element which applies the power for heat generation as thermal energy to a living tissue, and a control section which performs constant temperature control on the power source for heat generation on the basis of temperature of the heating element, and controls the power source for heat generation so as to finish application of the thermal energy and complete treatment if the power for heat generation becomes not more than predetermined threshold power which is independent of a type of the living tissue or if a rate of decrease in the power for heat generation becomes not more than a predetermined threshold rate.

An actuation method for a treatment system according to another embodiment includes a step of setting a treatment condition for the treatment system including a grasping member which applies thermal energy to a living tissue, a power source for heat generation which outputs power for heat generation for applying the thermal energy, and a control section, a step of controlling, by the control section, the power source for heat generation to start application of the thermal energy to the living tissue under constant temperature control based on the treatment condition, and a step of controlling, by the control section, the power source for heat generation to finish application of the thermal energy if the power for heat generation becomes not more than predetermined threshold power which is independent of a type of the living tissue or if a rate of decrease in the power for heat generation becomes not more than a predetermined threshold rate.

DETAILED DESCRIPTION OF THE PREFERRED EMBODIMENTS

<First Embodiment>
<Configuration of Treatment System>

A treatment system 10 according to a first embodiment will first be described.

Figure 1:
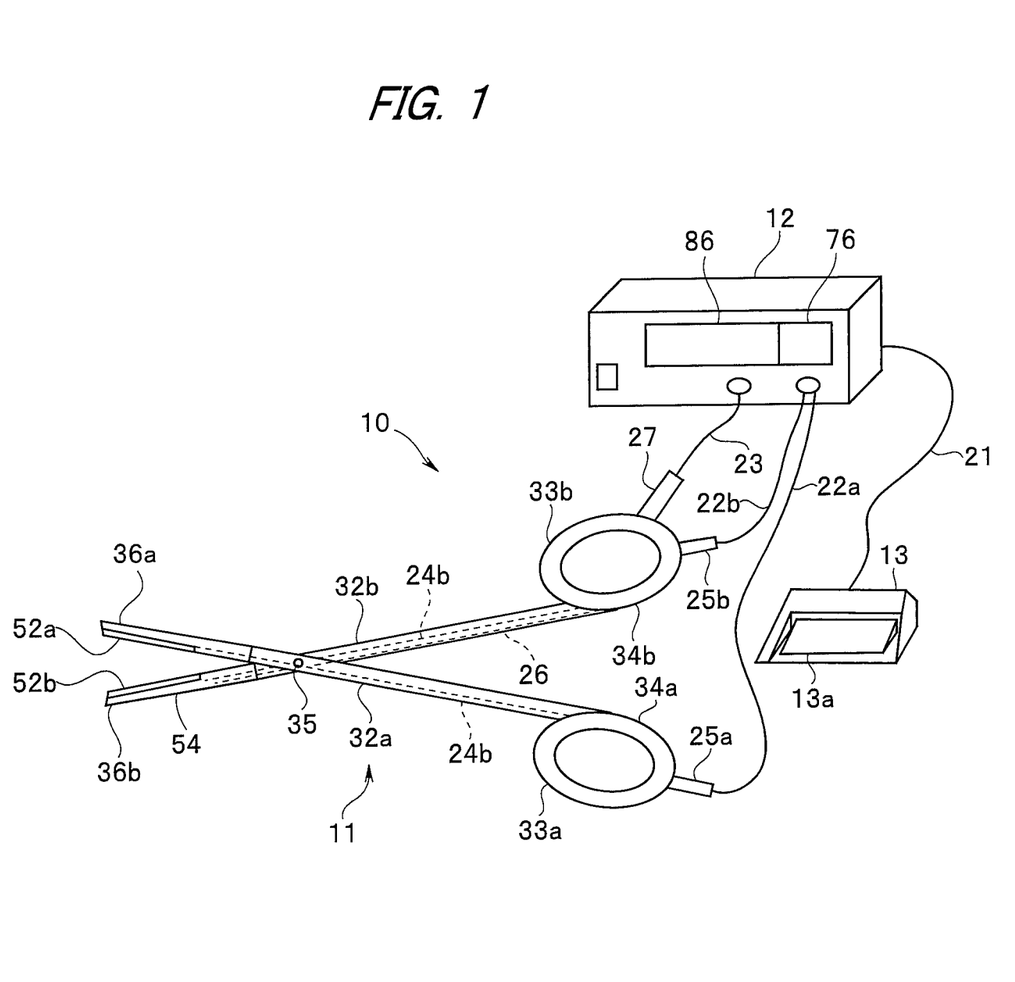
FIG. 1 is an external view of a treatment system according to a first embodiment.

As shown in FIG. 1, the treatment system 10 includes a treatment instrument 11, a power supply portion 12, and a foot switch 13. The treatment system 10 switches between high-frequency power energy and thermal energy and applies, using the power supply portion 12, the energy to a living tissue grasped by jaws 36a and 36b which are one pair of grasping members of the treatment instrument 11. Note that high-frequency power and power for heat generation may hereinafter be abbreviated as "HF" and "TH," respectively. For example, high-frequency power energy is referred to as HF energy.

The treatment instrument 11 is connected to the power supply portion 12 by HF lines 22a and 22b and a TH line 23. Note that although the HF lines 22a and 22b, the TH line 23, and the like each have two pieces of wiring, the two pieces of wiring are expressed as one line. The foot switch 13 is connected to the power supply portion 12 by a switch line 21.

The treatment instrument 11 has one pair of scissors constituent members 32a and 32b, one pair of handle portions 34a and 34b, and the one pair of jaws 36a and 36b. The handle portions 34a and 34b are provided at proximal end portions of the scissors constituent members 32a and 32b. The handle portions 34a and 34b are operated while being held in a hand by a surgeon. The jaws 36a and 36b are provided at distal end portions of the scissors constituent members 32a and 32b to grasp a living tissue to be treated.

The scissors constituent members 32a and 32b are placed one on the other so as to substantially intersect each other between distal ends and proximal ends of the scissors constituent members 32a and 32b. A fulcrum pin 35 which pivotably couples the scissors constituent members 32a and 32b is provided at an intersection portion of the scissors constituent members 32a and 32b.

The handle portions 34a and 34b are provided with rings 33a and 33b on which a surgeon puts his or her fingers. When the surgeon puts a thumb and a middle finger through the rings 33a and 33b, respectively, and opens and closes the rings 33a and 33b, the jaws 36a and 36b open and close in tandem with the motion.

Respective energy release elements which apply energy to a grasped living tissue are disposed at the jaws 36a and 36b. That is, an electrode 52a as the energy release element which has a grasping surface and is made of an electric conductor is disposed at the jaw 36a. An electrode 52b as the energy release element which has a grasping surface and is made of an electric conductor and a heater member 53 as a heating element are disposed at the jaw 36b. The heater member 53 is embedded in the jaw 36b while the heater member 53 is disposed on a reverse surface of the electrode 52b that is made of a high thermal conductor.

Figure 2:
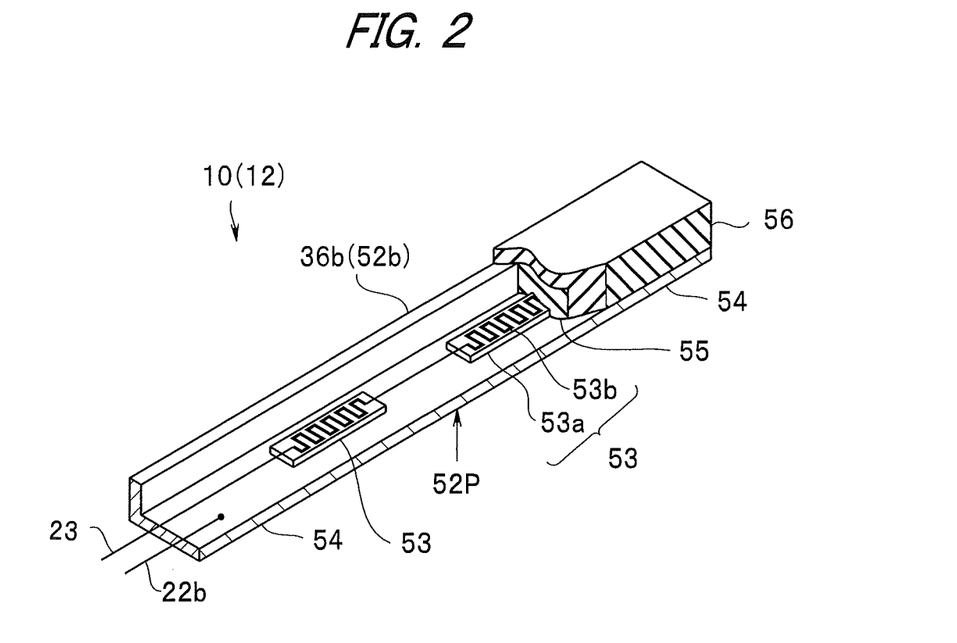
FIG. 2 is a three-dimensional cross-sectional view for explaining a structure of a jaw in the treatment system according to the first embodiment.

That is, as shown in FIG. 2, in the jaw 36b of the treatment instrument 11, the heater member 53 is joined to a surface reverse to a grasping surface 52P of a base 54 which is made of copper. The heater member 53 is covered with a sealing member 55 and a cover member 56. Note that FIG. 2 shows a portion of the jaw 36b and that three or more heater members 53 may be joined to each jaw 36b.

In the heater member 53, a thin-film resistor or a thick-film resistor is disposed as a heating pattern 53b on a substrate 53a of, e.g., alumina or aluminum nitride. The thin-film resistor is made of, e.g., an electrically conductive thin film which is formed by a thin film formation method, such as PVD (physical vapor deposition) or CVD (chemical vapor deposition), or foil of an electrically conductive metal, such as SUS. The thick-film resistor is formed by a thick film formation method, such as screen printing. The heating pattern 53b is formed of a refractory metal material, such as molybdenum, which exhibits a positive temperature coefficient of resistance indicating that electric resistance increases directly with temperature.

Note that the heater member 53 may also be disposed at the jaw 36a of the treatment instrument 11. That is, a heating element only needs to be disposed at at least one grasping member.

HF lines 24a and 24b for supplying HF to the electrodes 52a and 52b are disposed inside the scissors constituent members 32a and 32b, respectively. The HF lines 24a and 24b extend from the jaws 36a and 36b to the handle portions 34a and 34b, respectively. HF terminals 25a and 25b are provided at the rings 33a and 33b, respectively. The HF terminals 25a and 25b are connected to the HF lines 24a and 24b, respectively. For the reason, when HF is supplied to the electrodes 52a and 52b while a living tissue is grasped by the jaws 36a and 36b, HF is passed through the living tissue between the electrodes 52a and 52b. In other words, HF energy is applied to the living tissue.

A TH line 26 for supplying TH to the heater member 53 is disposed inside the scissors constituent member 32b. The TH line 26 extends from the jaw 36b to the handle portion 34b. A TH terminal 27 which is connected to the TH line 26 is provided at the ring 33b. For the reason, when TH is supplied to the heater member 53 through the TH line 26, the heater member 53 generates heat. That is, the TH is converted into thermal energy by the heater member 53, the thermal energy is transferred to the electrode 52b, and the thermal energy is applied to a living tissue in contact with the grasping surface of the electrode 52b.

As described above, when HF is passed between the electrodes 52a and 52b, the treatment instrument 11 applies HF energy to a living tissue grasped between the jaws 36a and 36b. When TH is passed through the heater member 53 in the treatment instrument 11, the TH is converted into the thermal energy. The treatment instrument 11 applies the thermal energy to the living tissue.

The foot switch 13 has a pedal 13a. While the pedal 13a is pressed, the power supply portion 12 outputs HF or TH on the basis of a setting state (a state in which an output value, output timing, and the like are controlled). When the press of the pedal 13a is canceled, the power supply portion 12 forcibly stops outputting the power.

Figure 3:
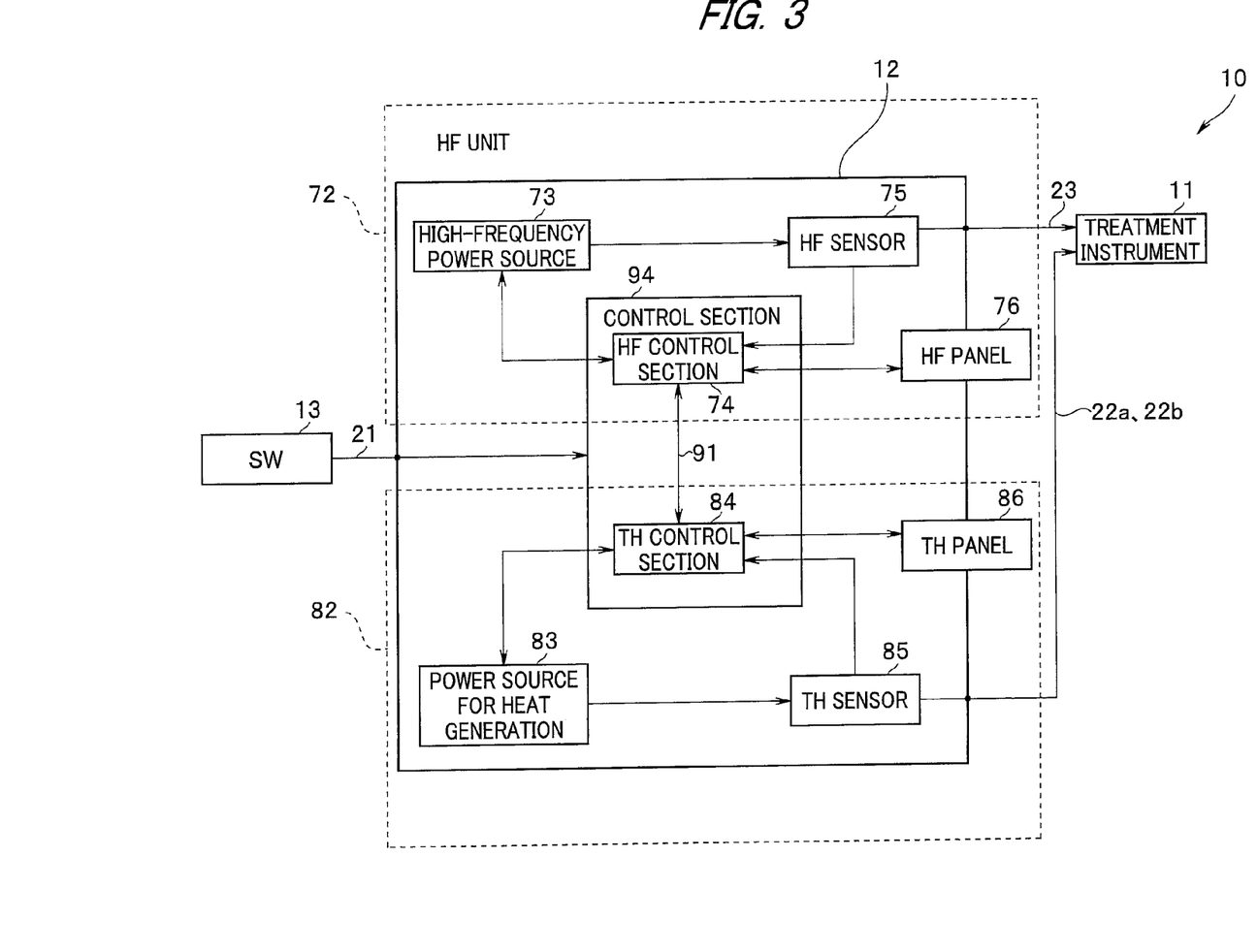
FIG. 3 is a configuration diagram of the treatment system according to the first embodiment.

As shown in FIG. 3, the power supply portion 12 is composed of an HF unit 72 and a TH unit 82. The HF unit 72 has a high-frequency power source 73 which outputs HF, an HF control section 74 made up of a computing circuit, such as a CPU which controls the high-frequency power source 73, an HF sensor 75 which is a high-frequency power measuring section which measures voltage and current of HF outputted by the high-frequency power source 73, and an operation panel 76.

The TH unit 82 has a power source 83 for heat generation which outputs TH, a TH control section 84 made up of a computing circuit, such as a CPU which controls the power source 83 for heat generation, a TH sensor 85 which is a heat generation power measuring section that measures voltage and current of TH outputted by the power source 83 for heat generation, and an operation panel 86.

The HF control section 74 and the TH control section 84 are connected by a communication line 91 which can transmit a signal in both directions to constitute a control section 94. That is, the control section 94 controls the high-frequency power source 73 and the power source 83 for heat generation. The operation panels 76 and 86 each have a setting function portion, with which a surgeon sets a treatment condition, and a display function of displaying a treatment status.

The HF sensor 75 is connected to the treatment instrument 11 via the HF lines 22a and 22b. The high-frequency power source 73 and the HF sensor 75 are connected to the HF control section 74. The HF control section 74 is further connected to the operation panel 76. The HF control section 74 calculates HF information, such as power and impedance, on the basis of information from the HF sensor 75, sends a control signal to the high-frequency power source 73, and sends information to be displayed to the operation panel 76. HF outputted by the high-frequency power source 73 that is controlled by the HF control section 74 is transmitted to the electrodes 52a and 52b of the treatment instrument 11.

The TH control section 84 calculates temperature of the heater member 53 as TH information on the basis of information from the TH sensor 85, in addition to power, a resistance value, and the like. That is, since the heating pattern of the heater member 53 is made of a material having a positive temperature coefficient of resistance, as already described, the TH control section 84 can calculate the temperature of the heater member 53 from a TH resistance value which is calculated from voltage and current of TH. The TH control section 84 sends a control signal to the power source 83 for heat generation on the basis of the TH information. TH outputted by the power source 83 for heat generation that is controlled by the TH control section 84 is transmitted to the heater member 53 of the treatment instrument 11.

Note that the HF control section 74 also sends a control signal to the TH control section 84 at the end of application of HF such that the TH control section 84 starts outputting TH.

As described above, the treatment instrument 11 has a function of a bipolar-type high-frequency treatment instrument and a function of a treatment instrument for heat generation.

Note that the treatment instrument of the treatment system according to the embodiment may be a so-called linear-type treatment instrument. For example, a treatment system 10A according to a modification shown in FIG. 4 includes a linear-type treatment instrument 11A, a power supply portion 12A, and the foot switch 13.

Figure 4:
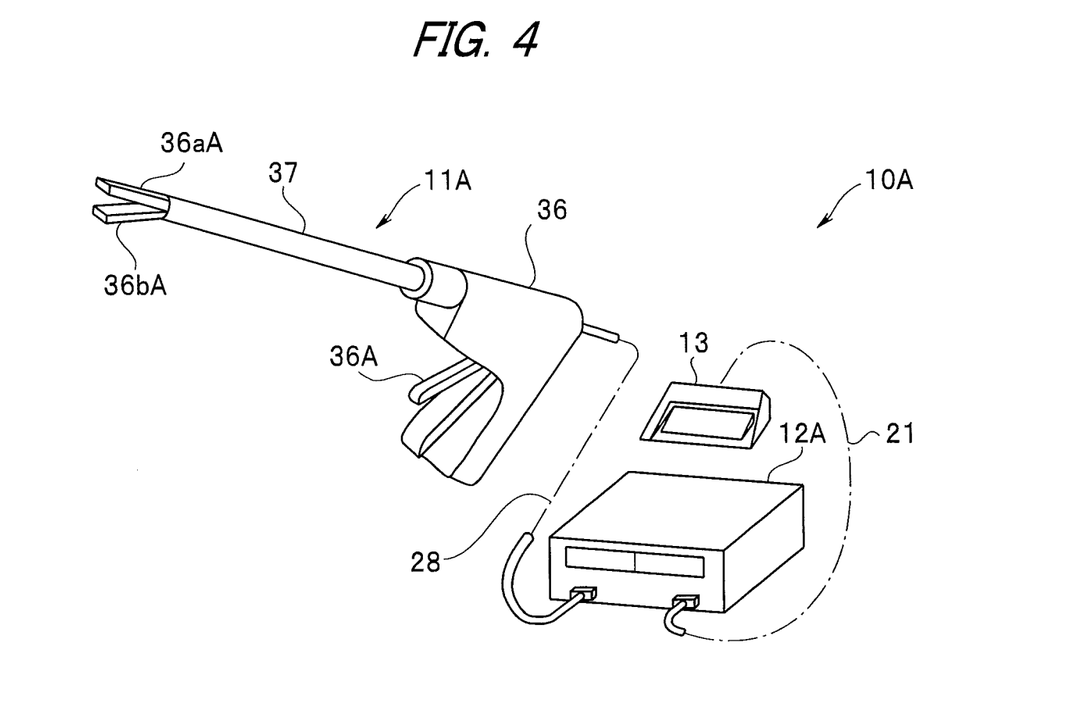
FIG. 4 is an external view of a treatment system according to a modification of the first embodiment.

The treatment instrument 11A has a handle 36, a shaft 37, and one pair of jaws 36aA and 36bA which are grasping members that grasp a living tissue. Structures of the jaws 36aA and 36bA are identical to the structures of the jaws 36a and 36b.

The handle 36 has a shape which is easy for a surgeon to grip, such as a substantially L-shape. The handle 36 has an open/close knob 36A. The open/close knob 36A is designed such that the jaws 36a and 36b grasp a living tissue when a surgeon presses and operates the open/close knob 36A. HF electrodes (not shown) and heater members (not shown) of the jaws 36aA and 36bA are connected to the power supply portion 12A via a piece 28 of wiring. That is, the piece 28 of wiring is made up of the HF lines 22a and 22b and the TH line 23. A basic configuration and a function of the power supply portion 12A are identical to the basic configuration and the function of the power supply portion 12.

That is, any of treatment instruments having various structures can be used as long as the treatment instrument can apply high-frequency power energy and thermal energy to a grasped living tissue.

<Motion of Treatment System>

An actuation method for the treatment system 10 will be described.

The treatment system 10 first applies HF energy to a grasped living tissue and applies thermal energy after the application of HF energy ends. In other words, the control section 94 controls the high-frequency power source 73 and the power source 83 for heat generation to start applying thermal energy after application of high-frequency power energy ends.

That is, the treatment system 10 switches from HF energy application mode to thermal energy application mode when a process of destroying cell membranes in the living tissue is completed by application of HF energy. In thermal energy application mode, moisture is removed by further raising temperature of the living tissue, and a process of joining the living tissue is performed through hydrogen bonding.

Treatment is completed by stopping application of thermal energy when the joining process is appropriately finished. Since the control section 94 (the TH control section 84) automatically finishes application of thermal energy in a proper time period, on the basis of change in TH, the treatment system 10 has good operability.

Figure 5:
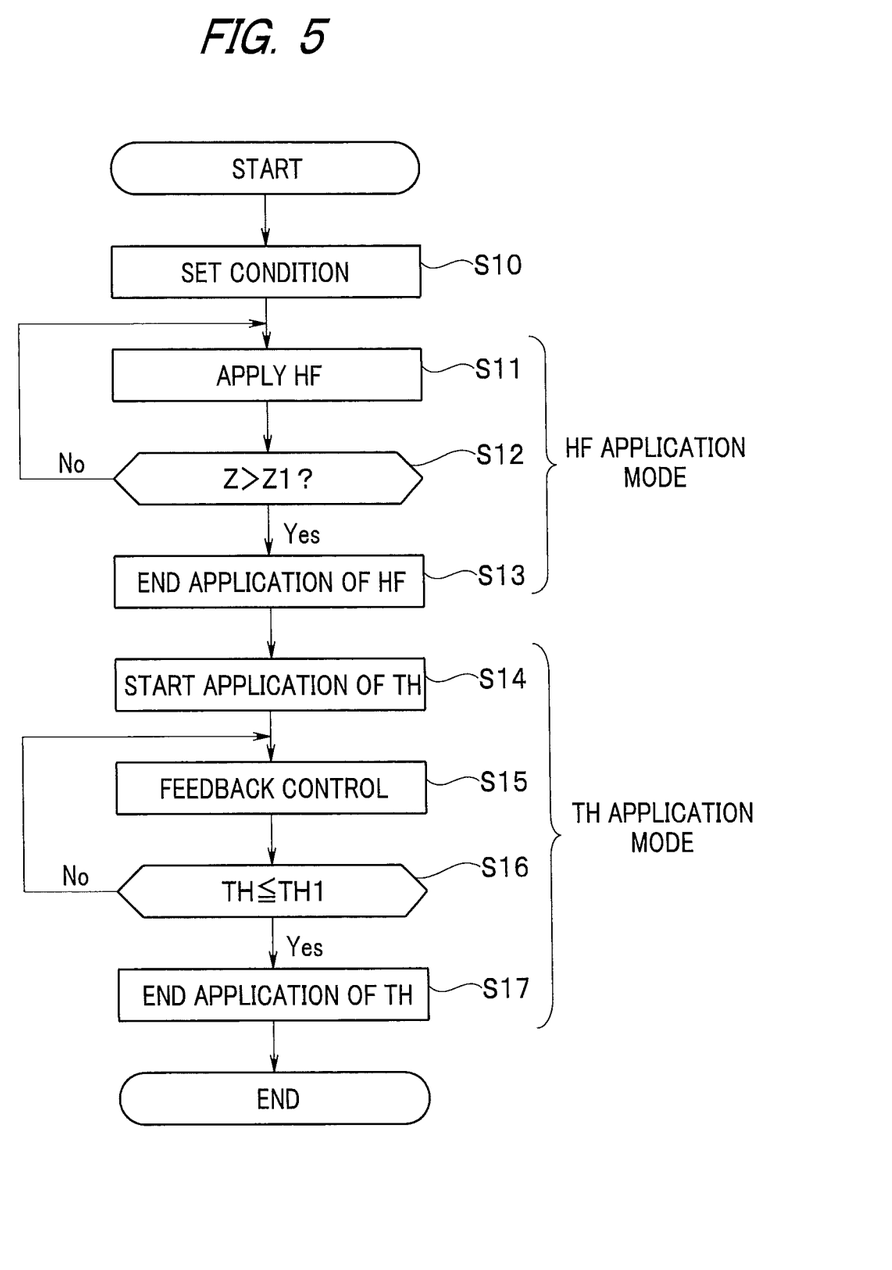
FIG. 5 is a flowchart for explaining a flow of processing of the treatment system according to the first embodiment.

A motion of the treatment system 10 will be described in detail below with reference to a flowchart shown in FIG. 5.

<Step S10>

A surgeon inputs and sets treatment conditions to the control section 94 by using the operation panels 76 and 86. Examples of the treatment conditions include setting power Pset (W) for HF energy application mode, setting voltage Vset (V), a setting temperature Tset (° C.) for thermal energy application mode, and a threshold value Z1 (Ω) for an HF impedance Z for determining when to end HF energy application mode. Note that the treatment conditions will be described in detail later.

<Step S11>

The surgeon puts his or her fingers on the rings 33a and 33b of the handle portions 34a and 34b of the treatment instrument 11, operates the treatment instrument 11, and grasps a living tissue to be treated with the jaws 36a and 36b.

When the surgeon presses the pedal 13a of the foot switch 13 with a foot, application of HF energy to the living tissue between the electrodes 52a and 52b of the jaws 36a and 36b of the treatment instrument 11 starts. Note that the pedal 13a remains pressed during treatment. When the surgeon takes the foot off the pedal 13a, the power supply portion 12 forcibly stops outputting the energy.

HF outputted by the high-frequency power source 73 is controlled by constant power control to a predetermined setting power Pset (e.g., about 20 W to 150 W) set in step S10.

In HF energy application mode, Joule heat is generated to heat the living tissue itself. Dielectric breakdown, electric discharge, and the like arising from HF action destroy cell membranes in the living tissue. With the destruction of the cell membranes, released materials from the cell membranes are uniformed with extracellular components typified by collagen.

Figure 6:
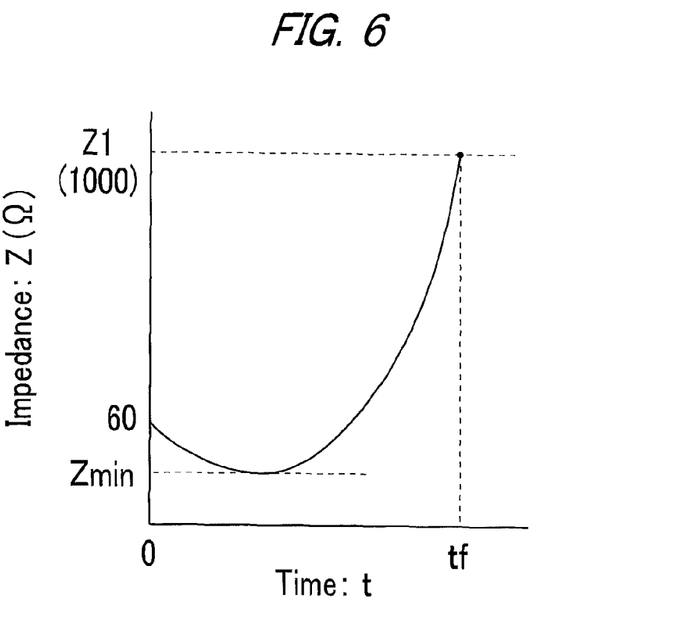
FIG. 6 is a graph showing change in impedance in high-frequency power application mode.

In HF energy application mode, the impedance Z for HF, i.e., the impedance Z in the grasped living tissue is calculated on the basis of HF information from the HF sensor 75. As shown in FIG. 6, the HF energy application under constant power control causes the impedance Z to be, for example, about 60Ω at the start of the HF energy application, decrease after the start to exhibit a minimum value Zmin, and increase after the exhibition.

<Step S12>

That is, since application of HF energy advances drying of the living tissue, the impedance Z for HF under constant power control rises. Completion of the process of destroying cell membranes in the grasped living tissue is sensed on the basis of the impedance Z. That is, since when the destruction process is completed, substances in cell membranes are released no longer, rise in the impedance Z accelerates. Additionally, when the impedance Z is high, appropriate HF energy application is difficult.

For the reason, the control section 94 (the HF control section 74) determines, on the basis of a predetermined threshold value Z1, whether to end HF energy application mode.

The threshold value Z1 is, for example, about 10Ω to 1500Ω. Note that the surgeon need not set the threshold value Z1 if the threshold value Z1 is incorporated in advance in a program of the control section 94 (the HF control section 74). Alternatively, whether to end HF energy application mode may be determined by another method.

The HF control section 74 determines whether the impedance Z has exceeded the threshold value Z1 (e.g., 1000Ω). If the HF control section 74 determines that a value of the impedance Z is less than the threshold value Z1 (NO in S12), the HF control section 74 continues applying HF energy.

<Step S13>

On the other hand, if the HF control section 74 determines that the impedance Z has exceeded the threshold value Z1 (YES in S12), the HF control section 74 controls the high-frequency power source 73 to stop outputting HF (t=tf).

<Step S14>

If the HF control section 74 determines that the impedance Z has become not less than the threshold value Z1, a signal is transmitted from the HF control section 74 of the HF unit 72 to the TH control section 84 of the TH unit 82 via the communication line 91. Switching from HF energy application mode to TH energy application mode is performed (t=0 (tf)).

Note that the HF control section 74 preferably finishes application of high-frequency power energy after more reliably completing the process of destroying cell membranes in the living tissue by changing HF energy application mode to constant voltage control (with the setting voltage Vset) before switching from HF energy application mode under constant power control (with the setting power Pset) to TH energy application mode. That is, a tissue having a complicated structure, such as a bronchus or a lung real tissue including a mixture of alveoli may have a site to which current can hardly flow under constant power control. HF under constant voltage control can effectively supply current even to such a site. It is thus possible to uniformly cauterize a grasped tissue.

Note that a time period for constant voltage control is preferably automatically determined according to a time period for constant power control. The time period for constant power control here refers to a time period to stop outputting HF under constant power control which is determined on the basis of the impedance Z. For example, the constant voltage control time period is set to 3 seconds if the constant power control time period is less than 4 seconds, is set to 4 seconds if the constant power control time period is not less than 4 seconds and less than 15 seconds, and is set to 5 seconds if the constant power control time period is not less than 15 seconds.

<Step S15>

In an initial stage of TH energy application mode, the TH control section 84 supplies TH to the heater member 53 such that the temperature of the heater member 53 is a predetermined setting temperature Tset (e.g., about 120° C. to 300° C.). That is, the TH control section 84 performs feedback control that increases/decreases TH output such that a temperature T of the heater member 53 is the temperature Tset set as the treatment condition in step S10.

The treatment in HF energy application mode has made the living tissue uniformed and has raised thermal conductivity. For the reason, in TH energy application mode, heat from the heater member 53 is efficiently transferred to the living tissue. In TH energy application mode, proteins in the living tissue are integrally denatured, and removal of moisture that is a hindrance to hydrogen bonding between proteins is performed.

Figure 7:
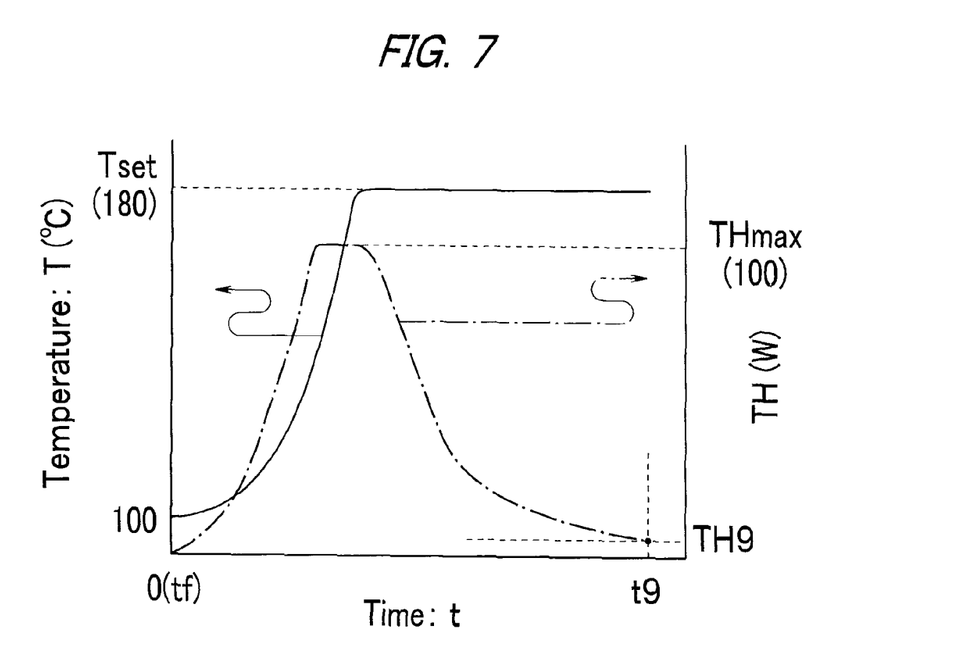
FIG. 7 is a graph showing change in temperature and change in power for heat generation in power-for-heat-generation application mode.

As shown in FIG. 7, the temperature T of the heater member 53 at a TH energy application mode start time, i.e., at an HF energy application mode finish time is, for example, 100° C. Application of power for heat generation that is brought under constant temperature control aiming for the setting temperature Tset causes the temperature T of the heater member 53 to rise to the setting temperature Tset (e.g., 180° C.) and then be held at the setting temperature Tset.

In contrast, power TH for heat generation is high until the temperature rises to the setting temperature Tset. In other words, since temperature of the grasped living tissue having high thermal capacity needs to be raised in order to raise the temperature T of the heater member 53, the TH needs to be high.

Note that the TH exhibits a fixed value (THmax) from a time t1 to a time t2 in FIG. 7 because the value THmax is set to a maximum rated power (e.g., 100 W) of the power source 83 for heat generation. The value THmax is set to the maximum rated power because a power source having high maximum rated power is expensive and large. Note that the treatment system 10 does not matter much even when an inexpensive power source having low maximum rated power is used.

After the temperature T of the heater member 53 reaches the setting temperature Tset, the TH required to maintain the temperature Tset becomes low. As the treatment advances further, and contraction or the like of the grasped living tissue advances, the TH becomes lower. That is, the TH increases after application of thermal energy starts and decreases after a maximum value is exhibited.

<Steps S16 and S17>

As already described, application of thermal energy needs to be finished at a proper time. However, since feedback control is performed on the basis of the temperature T of the heater member 53 in TH energy application mode in the treatment system 10, change in status of the grasped living tissue cannot be monitored directly from change in temperature.

The control section 94 here monitors TH (an output value) which is detected by the TH sensor 85 for feedback control. In the treatment system 10, the control section 94 controls the power source 83 for heat generation on the basis of the TH (output value) being monitored so as to finish application of thermal energy.

Application of thermal energy to a living tissue for more than a proper time period not only brings about no improvement in effectiveness but also has adverse effects, such as adherence of the living tissue to a treatment surface. For the reason, application of thermal energy needs to be finished at a proper time. Proper application finish times, however, vary according to the type, size, and the like of a living tissue being treated. A user thus needs to monitor a treatment status and finish application of thermal energy on the basis of experience and the like.

The inventor has found that proper treatment can be performed by finishing application of thermal energy when TH becomes not more than predetermined threshold power, even if the type, size, moisture content, and the like of a living tissue being processed are different.

As shown in FIG. 7, when the TH becomes not more than predetermined threshold power TH9 (YES in S16), the control section 94 (the TH control section 84) of the treatment system 10 controls the power source 83 for heat generation in step S17 (time t=t9) so as to finish application of thermal energy. On the other hand, if the TH is less than the predetermined power TH9 (NO in S16), the control section 94 continues feedback control from step S15.

The threshold power TH9 is preferably 5 W to 30 W, particularly preferably 15 W to 25 W. If the threshold power TH9 is within the range, application of thermal energy can be automatically finished at a proper time.

The threshold power TH9 is inputted and set to the control section 94 by a surgeon using the operation panels 76 and 86, like the threshold value Z1. Note that the surgeon need not set the threshold power TH9 if the threshold power TH9 is incorporated in advance in a program of the control section 94.

Figure 8:
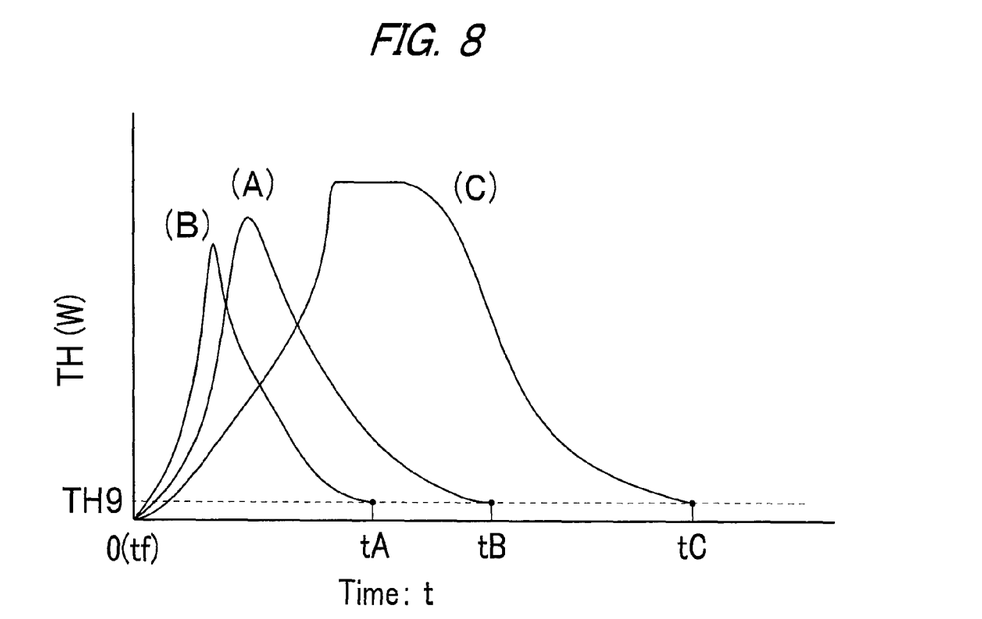
FIG. 8 is a graph showing change in power for heat generation in power-for-heat-generation application mode.

As shown in FIG. 8, proper times for finishing application of thermal energy vary greatly according to the type and the like of a grasped living tissue. For example, curve (A) is for a tubular organ, such as a small intestine or a large intestine, curve (B) is for a blood vessel, and curve (C) is for a parenchyma organ, such as a lung, a liver, or a pancreas. That is, in the case of a tissue having low thermal capacity, application of thermal energy needs to be finished in a short time period. In contrast, a tissue having high thermal capacity requires application of thermal energy for a longer time period.

The treatment system 10 finishes application of thermal energy at a time to in the case of (A), finishes application of thermal energy at a time tB in the case of (B), and finishes application of thermal energy at a time tC in the case of (C), on the basis of a value of the TH monitored.

That is, the treatment system 10 and the actuation method for the treatment system 10 are capable of removing moisture from a living tissue and joining the living tissue through hydrogen bonding and then automatically completing treatment in an appropriate manner without applying excessive heat to the living tissue, even if the type and the like of the grasped living tissue are different. The treatment system 10 and the actuation method for the treatment system 10 are thus good in operability.

Figure 9:
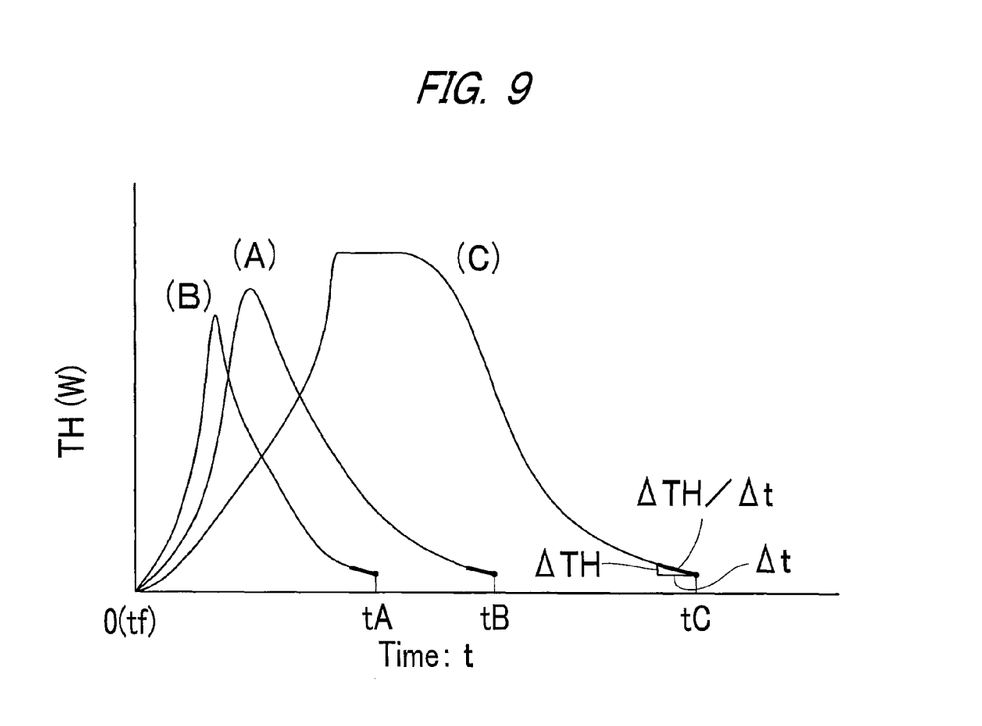
FIG. 9 is a graph showing change in power for heat generation in power-for-heat-generation application mode.

Note that the control section 94 (TH control section 84) may control the power source 83 for heat generation so as to finish application of thermal energy when a rate ($\Delta TH/\Delta At$) of decrease in power (TH) for heat generation, i.e., slope of a curve of decrease in TH becomes not more than a predetermined threshold rate (a predetermined slope), as shown in FIG. 9. Control using a rate of decrease in TH as a parameter is less likely to cause misoperation due to, e.g., noise than control using a value of TH as a parameter.

<First Modification of First Embodiment>

Figure 10:
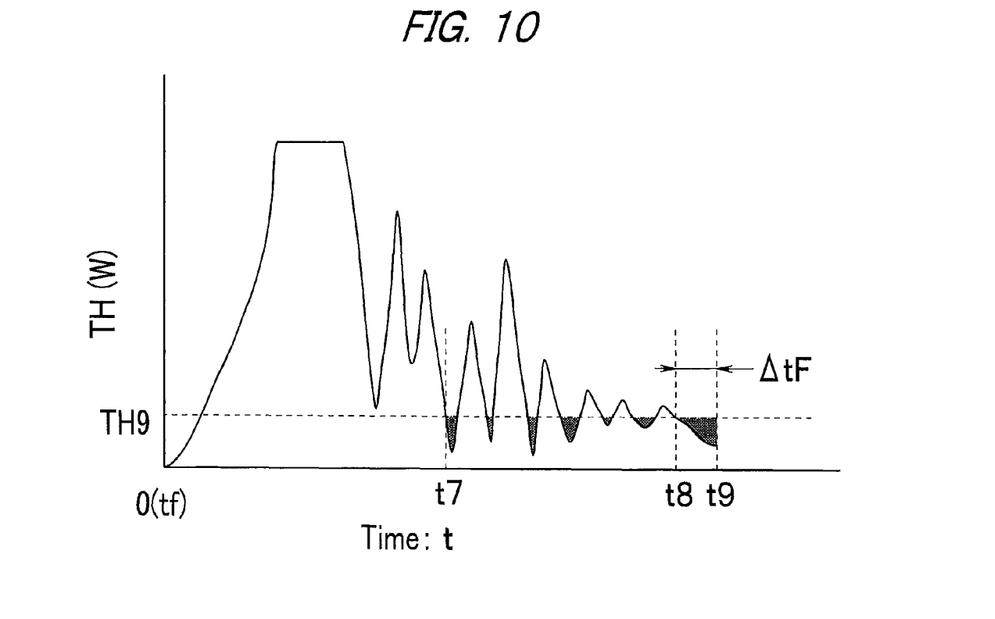
FIG. 10 is a graph showing change in power for heat generation in power-for-heat-generation application mode.

As shown in FIG. 10, TH may not monotonically decrease but may decrease with repetition of increase and decrease, depending on the type and a grasping status of a grasped living tissue, effects of contact with a surrounding tissue, or the like. In the case, the control section 94 (the TH control section 84) may erroneously finish application of thermal energy when the TH becomes not more than predetermined threshold power TH9 for a first time (t=t7).

In order to prevent such misoperation, the control section 94 preferably controls the power source 83 for heat generation so as to finish application of thermal energy at a time (t9) when the TH has continued to be not more than the threshold power TH9 for a first predetermined time period $\Delta tF$ or longer. That is, application of thermal energy is finished at the time (t=t9) after a lapse of the first predetermined time period $\Delta tF$ from a time (t=t8) when the TH becomes not more than the threshold power TH9.

For example, even if the TH becomes not more than the threshold power TH9 at the time (t=t7), the control section 94 controls the power source 83 for heat generation so as to continue application of thermal energy if the T exceeds the threshold power TH9 in a time period less than the first predetermined time period $\Delta tF$.

The first predetermined time period $\Delta tF$ is preferably within the range of 0.05 seconds to 2 seconds (e.g., 0.2 seconds). If the first predetermined time period $\Delta tF$ is within the range, it is possible to prevent application of thermal energy from being erroneously finished due to, e.g., disturbance and appropriately complete treatment.

Note that the control section 94 may perform control on the basis of a moving average of TH output values detected by the TH sensor 85 or suitably adjust a time constant for detection of the TH sensor 85, in order to prevent misoperation due to incremental/decremental change in TH.

Even in the case of control using a rate of decrease in TH as a parameter, similarly, the control section 94 preferably controls the power source 83 for heat generation so as to finish application of thermal energy in, e.g., a case where the TH continues to be not more than a predetermined threshold rate for a second predetermined time period tM2 or longer.

<Second Modification of First Embodiment>

As described above, the treatment system 10 automatically finishes application of thermal energy. However, application of thermal energy may not be finished by automatic control for some reasons.

For the reason, the treatment system 10 preferably has a forcible finishing function, in addition to the ordinary automatic finishing function already described.

Figure 11:
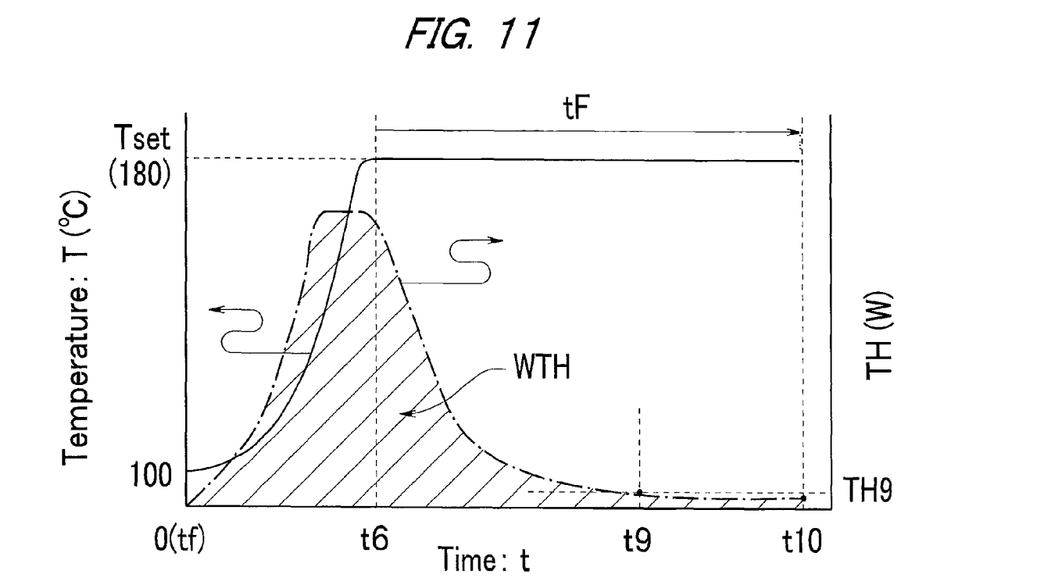
FIG. 11 is a graph showing change in temperature and change in power for heat generation in power-for-heat-generation application mode.

Various actuation methods for forcibly finishing application of thermal energy will be described with reference to FIG. 11. FIG. 11 shows a case where application of thermal energy continues even after TH reaches threshold power TH9 at a time t9.

In first forcible finishing control, the control section 94 controls the power source 83 for heat generation so as to finish application of thermal energy at a time (t10) when an integrated value WTH of the TH becomes not less than a predetermined threshold integrated value. The integrated value WTH indicated by a hatched region in FIG. 11 is the total amount of TH outputted after application of thermal energy starts. The integrated value WTH is computed by, for example, an internal memory (not shown) which is made up of, e.g., a semiconductor memory of the control section 94.

In second forcible finishing control, the control section 94 controls the power source 83 for heat generation so as to finish application of thermal energy at a time (t10) when an elapsed time period since a time (t6) when temperature of the heater member 53 serving as a heating element becomes not less than a setting temperature Tset (° C.) becomes not less than a predetermined threshold time period tF.

The treatment system 10 having the energy application forcible finishing function has better operability.

Note that, in the second forcible finishing control, the threshold time period tF is preferably automatically determined according to a time period for constant power control in HF application mode. For example, the threshold time period tF is set to 3 seconds if the constant power control time period is less than 4 seconds, is set to 5 seconds if the constant power control time period is not less than 4 seconds and less than 15 seconds, and is set to 10 seconds if the constant power control time period is not less than 15 seconds.

The second forcible finishing control according to a time period for constant power control here can be used not only as forcible control means in a case where ordinary control does not function normally but also as control means for finishing application of thermal energy at a proper time, as in ordinary control. That is, application of thermal energy can be finished at a proper time by appropriately selecting the threshold time period tF, as in ordinary control.

<Second Embodiment>

A treatment system 10B according to a second embodiment will be described. Since the treatment system 10B is similar to the treatment system 10, constituent elements having identical functions are denoted by identical reference numerals, and a description of the constituent elements will be omitted.

Figure 12:
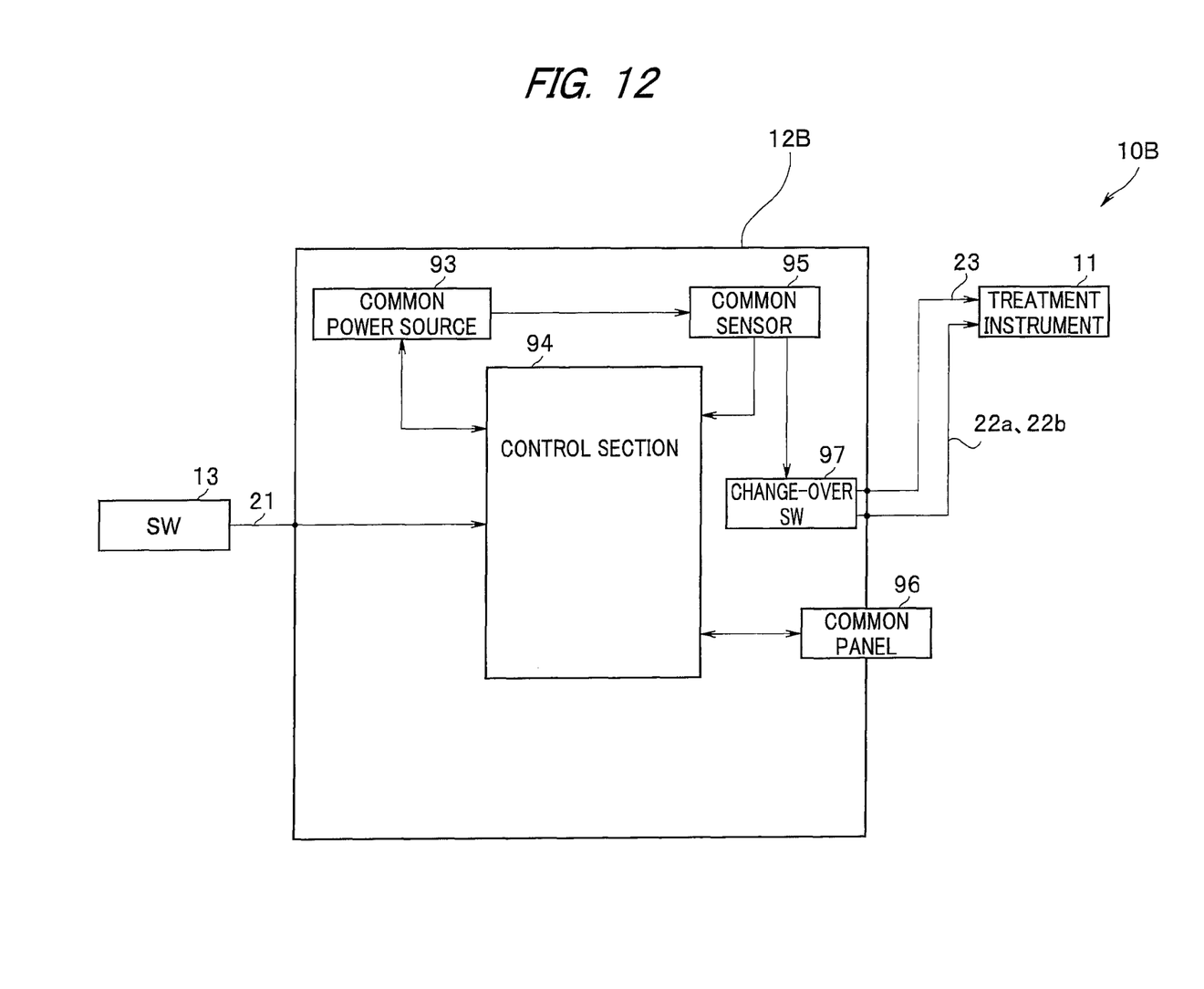
FIG. 12 is a configuration diagram of a treatment system according to a second embodiment.

As shown in FIG. 12, a power supply portion 12B of the treatment system 10B has a common power source 93 which has a high-frequency power source function and a power-source-for-heat-generation function and a change-over switch 97 which switches an output destination. The power supply portion 12B further has a common sensor 95 which has the function of an HF sensor 75 and the function of a TH sensor 85.

As already described, the high-frequency power source 73 and the power source 83 for heat generation do not simultaneously output power even in the treatment system 10 according to the embodiment. For the reason, in the treatment system 10B, the one common power source 93 functions as a high-frequency power source or a power source for heat generation under control of a control section 94.

That is, in HF application mode, HF outputted by the common power source 93 is sent to HF lines 22a and 22b via the change-over switch 97. In TH application mode, TH outputted by the common power source 93 is sent to the TH line 23 via the change-over switch 97.

Note that the common sensor 95 functions as an HF sensor or a TH sensor and that a common panel 96 functions as an HF panel or a TH panel.

The treatment system 10B and an actuation method for the treatment system 10B have the same function as effects of the treatment system 10 and the like and are simple in configuration.

Note that, in a treatment system in which respective heater members are disposed at jaws 36a and 36b of a treatment instrument 11, respective power sources for heat generation may be controlled on the basis of temperatures of the heater members. Alternatively, control may be performed by one power source for heat generation on the basis of an average temperature of the two heater members.

A treatment system according to an embodiment includes a high-frequency power source which outputs high-frequency power, a power source for heat generation which outputs power for heat generation, one pair of grasping members having one pair of electric conductors which apply the high-frequency power as high-frequency power energy to a grasped living tissue and are disposed at respective grasping surfaces of the two grasping members and a heating element which applies the power for heat generation as thermal energy to the living tissue, is disposed at at least one of the grasping members, and is made of a material having a positive temperature coefficient of resistance, and a control section which controls the high-frequency power source and the power source for heat generation after application of the high-frequency power energy finishes so as to start application of the thermal energy, and performs constant temperature control on the power source for heat generation on the basis of temperature of the heating element and performs control so as to finish application of the thermal energy if the power for heat generation, which increases after application of the thermal energy starts and decreases after a maximum value is exhibited, becomes not more than threshold power or if a rate of decrease in the power for heat generation becomes not more than a threshold rate, after application of the thermal energy starts.

A control method for a treatment system according to another embodiment includes a step of setting a treatment condition for the treatment system including one pair of grasping members which apply high-frequency power energy and thermal energy to a grasped living tissue, a high-frequency power source which outputs high-frequency power for applying the high-frequency power energy, and a power source for heat generation which outputs power for heat generation for applying the thermal energy, a step of controlling the high-frequency power source on the basis of the treatment condition to apply the high-frequency power energy to the living tissue, a step of starting application of the thermal energy under constant temperature control based on the treatment condition after application of the high-frequency power energy is finished on the basis of the treatment condition, and a step of finishing application of the thermal energy if the power for heat generation that increases after application of the thermal energy starts and decreases after a maximum value is exhibited becomes not more than threshold power or if a rate of decrease in the power for heat generation becomes not more than a threshold rate, under the constant temperature control.

The present invention is not limited to the above-described embodiments and the like. Various changes, modifications, and the like can be made without departing from the scope of the present invention.

What is claimed is:

1. A treatment system comprising:
a power source for heat generation which outputs power for heat generation;
a grasping member having a heating element which applies the power for heat generation as thermal energy to a living tissue; and
a controller comprising hardware configured to calculate a temperature of the heating element from a resistance of the heating element and to perform temperature control on the power source for heat generation on the basis of temperature of the heating element;
wherein the temperature control comprising a first phase during which application of the power of the heating element causes the temperature of the heating element to rise to a predetermined setting temperature and a second phase, subsequent to the first phase, during which application of the power for heat generation causes the temperature of the heating element to maintain at the predetermined setting temperature;
wherein the controller, during the second phase, controls the power source for heat generation to:
decrease the power for heat generation to maintain the temperature of the heating element at the predetermined setting temperature; and
shut off the power for heat generation to finish application of the thermal energy and complete treatment if a rate of decrease in the power for heat generation becomes not more than a predetermined threshold rate.

2. The treatment system according to claim 1, further comprising
a high-frequency power source which outputs high-frequency power, wherein
the grasping member has an electric conductor which applies the high-frequency power as high-frequency power energy, and
the control section controls the high-frequency power source and the power source for heat generation after application of the high-frequency power energy finishes so as to start application of the thermal energy, and
controls the high-frequency power source so as to finish application of the high-frequency power energy after performing constant voltage control after constant power control and completing a process of destroying a cell membrane in the living tissue, at a time of application of the high-frequency power energy.

3. The treatment system according to claim 2, wherein the high-frequency power source and the power source for heat generation are made up of a common power source.

4. A treatment system comprising:
a power source for heat generation which outputs power for heat generation;

a grasping member having a heating element which applies the power for heat generation as thermal energy to a living tissue; and a controller comprising hardware configured to:
  process at least information of a threshold power, the threshold power being a characteristic of a moisture content of the living tissue which decreases upon application of the thermal energy to the living tissue;
  calculate a temperature of the heating element from a resistance of the heating element; and
  perform temperature control on the power source for heat generation on the basis of the temperature of the heating element and at least the information of the threshold power;

wherein the temperature control comprising a first phase during which application of the power of the heating element causes the temperature of the heating element to rise to a predetermined setting temperature and a second phase, subsequent to the first phase, during which application of the power for heat generation causes the temperature of the heating element to maintain at the predetermined setting temperature;

wherein the controller, during the second phase, controls the power source for heat generation to:
  decrease the power for heat generation to maintain the temperature of the heating element at the predetermined setting temperature; and
  shut off the power for heat generation to finish application of the thermal energy and complete treatment if the power for heat generation becomes not more than the threshold power.

5. The treatment system according to claim 4, further comprising
  a high-frequency power source which outputs high-frequency power, wherein
  the grasping member has an electric conductor which applies the high-frequency power as high-frequency power energy, and
  the control section controls the high-frequency power source and the power source for heat generation after application of the high-frequency power energy finishes so as to start application of the thermal energy, and
  controls the high-frequency power source so as to finish application of the high-frequency power energy after performing constant voltage control after constant power control and completing a process of destroying a cell membrane in the living tissue, at a time of application of the high-frequency power energy.

6. The treatment system according to claim 5, wherein the high-frequency power source and the power source for heat generation are made up of a common power source.

* * * * *